United States Patent [19]

Bianchini

[11] Patent Number: 4,629,699

[45] Date of Patent: Dec. 16, 1986

[54] PROCESS FOR THE PREPARATION OF OLIGOSACCHARIDE FRACTIONS BY DEGRADATION OF HEPARIN

[75] Inventor: Pietro Bianchini, Corlo, Italy

[73] Assignee: Opocrin S.p.A., Pacinotti-Corlo, Italy

[21] Appl. No.: 582,933

[22] Filed: Feb. 23, 1984

[30] Foreign Application Priority Data

Mar. 8, 1983 [IT] Italy .............................. 40021 A/83

[51] Int. Cl.$^4$ ...................... C12P 19/04; C12P 19/26; C07H 37/00
[52] U.S. Cl. ...................................... 435/101; 536/21; 536/123; 536/18.7
[58] Field of Search .................. 435/101; 536/21, 123, 536/18.7

[56] References Cited

U.S. PATENT DOCUMENTS

| | | | |
|---|---|---|---|
| 4,281,108 | 7/1981 | Fussi | 536/21 |
| 4,303,651 | 12/1981 | Lindahl et al. | 536/21 |
| 4,351,938 | 9/1982 | Barnett | 536/21 |
| 4,401,662 | 8/1983 | Lormeau et al. | 536/21 |
| 4,474,770 | 10/1984 | Lormeau et al. | 536/21 |
| 4,500,519 | 2/1985 | Lormeau et al. | 536/21 |

*Primary Examiner*—Johnnie R. Brown
*Attorney, Agent, or Firm*—Bucknam and Archer

[57] ABSTRACT

Process for the preparation of oligosaccharides and oligosaccharide fractions by degradation of heparin, which comprises submitting to incubation an aqueous solution of heparin containing from 5 to 30 g of heparin/liter in the presence of 4–50 m.moles/1 of cupric acetate and 50–300 m.moles/1 of hydrogen peroxide, at a temperature of 40°–50° C., for 20–24 hours and keeping the pH at a value of 7.8 by means of sodium acetate.

The obtained products show a high inhibiting property of the Xa factor, a high antithrombotic activity and a very modest anticoagulant activity; therefore they are very interesting for a possible utilization as drugs in the antithrombotic treatment, practically free from any risk of haemorrhages.

3 Claims, No Drawings

PROCESS FOR THE PREPARATION OF OLIGOSACCHARIDE FRACTIONS BY DEGRADATION OF HEPARIN

The present invention refers to a chemical process for the preparation of oligosaccharide fractions having interesting biological activities starting from heparin.

The invention embraces also the so obtained oligosaccharide fractions.

It is known that oligosaccharides and oligosaccharide fractions containing the same, derived from heparin, show an interesting anti Xa activity of the blood, which is believed to correspond to a high antithrombotic activity associated with a relatively low anticoagulant activity. Such oligosaccharides and/or oligosaccharide fractions containing the same have a relatively low average molecular weight, about 5,000 Daltons. They are obtained from heparin by means of degradation processes, commonly defined as depolymerization processes, having the purpose of producing fragments of molecular weights lower than those of the starting heparin. Said processes are substantially of two types: enzymatic and chemical. The known chemical processes include the treatment with nitrous acid, the oxidation by means of peroxides carried out both under atmospheric and higher pressure and the oxidation by means of periodates.

S. E. Lasker in "Low molecular-weight derivative of heparin that is orally active in mice" in Adv. Exp. Med. and Biol. Vol. 52 "Heparin Structure Function and Clinical implications" p. 119–130 Plenum Press N.Y. (1975) has described a process which comprises depolymerizing the heparin by incubation at 40° C. for 24 hours of its aqueous solution in the presence of ascorbic acid and cupric sulphate. According to the same author, it is possible and even preferred, in order to avoid the pollution of the product induced by cupric ions, to substitute the cupric sulphate with a 3% solution of hydrogen peroxide.

Nevertheless it has been experimentally found that, apart from the pollution due to the copper, the depolymerization of the heparin carried out in the presence of ascorbic acid and cupric sulphate leads to oligosaccharide fractions having an average molecular weight still very high, usually higher than 9,200 Daltons.

It is clear that in order to isolate the most interesting fractions from this oligosaccharide mixture i.e., those having an average molecular weight ranging from 4,000 to 5,000, it is necessary to carry out fractionations by means of solvents, particularly ethanol, as described by Lasker same with a consequent considerable lowering of yields of useful product.

Also the depolymerization carried out in the presence of ascorbic acid and a 3% solution of hydrogen peroxide (the latter in substitution of the cupric sulphate) leads to oligosaccharide fractions having a high average molecular weight of about 11,500 Daltons, scarcely utilizable for the preparation, by means of fractionation of oligosaccharide fractions having the desired average molecular weight.

Also the depolymerization carried out by combining both the above cited techniques, which is carried out in the presence of ascorbic acid, cupric sulphate and a 3% solution of hydrogen peroxide, leads to fractions having an average molecular weight higher than 9,000 Daltons. The above cited combination of operative conditions (cupric sulphate and hydrogen peroxide) is not indicated, not even suggested by Lasker in his above mentioned work. Nevertheless, the depolymerization in such conditions has been considered a possible improvement of the single Lasker processes.

By repeating experimentally the process which employ copper, it could be confirmed that they lead to oligosaccharide fractions irreversibly polluted by cupric ions.

It has now surprisingly been found that it is possible to obtain directly oligosaccharide fractions having an average molecular weight very close to the desired one by means of the process for the degradation of heparin which is the object of the present invention and which comprises incubating an aqueous solution of heparin containing from 5 to 20 g of heparin per liter, in the presence of 4–50 m.moles/l of ascorbic acid, 0.4–2.5 m.moles/l of cupric acetate and 50–300 m.moles/l of hydrogen peroxide at a temperature of 40°–50° C. for 20–24 hours and maintaining the pH at a value of 7.5–8 by means of sodium acetate.

The best results are obtained by incubating an aqueous solution of heparin containing 10 g of heparin per liter, in the presence of 20 m.moles/l of ascorbic acid, of 2.25 m.moles of cupric acetate and of 180 m.moles of hydrogen peroxide at a temperature of about 50° C. for 24 hours and at a pH of 7.8.

In comparison with the known methods the process of the present invention allows to obtain oligosaccharide fractions having an average molecular weight which does not require any further fractionation procedure. The obtained products, furthermore, are not irreversibly polluted by residuals of cupric ions.

Occasional traces of cupric compounds can easily be removed through dissolution in water, addition of chelating agents such as, for instance, EDTA and precipitation from suitable solvents.

If desired, it is possible to submit the oligosaccharides obtained by means of the process of the present invention to purification and/or fractionation processes, known in the art. It is therefore possible to obtain products whose biological activities are further enhanced.

Although it is possible to carry out the process of the present invention within rather wide ranges of concentrations, the best results, with reference both to the average molecular weight of the obtainable oligosaccharide fractions and to their biological properties, are achieved by operating at concentrations comprised between 5 and 10 g of heparin per liter of solution, by maintaining substantially constant the molar ratios of the various reagents with reference to the heparin.

In order to keep the pH suitable for carrying out the depolymerization process, different buffering agents can be used: nevertheless it has been found that the sodium acetate gives the most satisfying results.

In fact it does not form with the cupric ions present in the solution those hardly reversible and scarcely soluble complexes which lead in turn to a pollution of the product.

The mixtures of oligosaccharides obtained according to the process of the present invention display a very low degree of anticoagulant activity, much lower than that displayed by the starting heparin. The anticoagulant activity of the oligosaccharide fractions obtained according to the process of the present invention, determined by means of the USP method (see the foot note on table 1) is only the 20-30% of the activity of the starting heparin.

The anticoagulant activity evaluated in vitro as APTT (see note as above) is reduced to 10–15% of that of the heparin.

On the contrary the activity inhibiting the Xa factor evaluated by means of the coagulometric method (see note as above) is reduced to 25–35% of that of the heparin, while, if evaluated by means of the cromogenic method (see the above note) it is reduced to the 55–60% of that of the heparin.

If one takes into consideration the ratio between the anti Xa activity evaluated by means of the cromogenic method and the APTT activity (anti Xa cr/APTT), as well as the ratio between the anti Xa activity evaluated by means of the coagulometric method and the APTT activity (anti Xa Co/APTT), it is possible to verify that, with respect to the heparin, these ratios are of about 0.6 for the anti Xa Cr/APTT, and of about 0.8 for the anti Xa Co/APTT.

For the products prepared by the process of the present invention, corresponding values of about 4 and about 2 respectively are obtained. This corresponds to a percent increase of about 600% and 250%.

The products obtained by the process of the present invention are thus able to considerably inhibit the Xa factor and, at the same time, possess a very poor anticoagulant activity. Accordingly, they are very interesting for the possible use as drugs for the antithrombotic treatment practically free from the risk of hemorrages.

The products of the present invention show an average molecular weight comprised between 3,000 and 6,000 Daltons.

The following examples are given only by way of illustration, but must not be considered as a limitation of the invention itself.

EXAMPLE 1

Commercial heparin having an average molecular weight of 13,500 Daltons and provided with the biological properties shown in table 1, was submitted to depolymerization according to the process of the present invention.

Grams 10 of heparin were dissolved in 700 ml of an aqueous solution containing g 30 (500 m.moles) of sodium chloride and 30 g (200 m.moles) of sodium acetate tri-hydrate ($CH_3COONa \cdot 3H_2O$). The pH was adjusted to 7.8 by means of NaOH 2N. The resulting solution was then added under stirring first with 200 ml of an aqueous solution containing 3.5 g (20 m.moles) of ascorbic acid, brought to a pH 7–7.5 by means of NaOH, and subsequently with 100 ml of an aqueous solution containing 0.45 g (2.25 m.moles) of cupric acetate monohydrate ($(CH_3COO)_2Cu \cdot H_2O$).

Finally 15 ml of 36% hydrogen peroxide (180 m.moles) were added always under stirring.

The pH was adjusted to 7.8 by means of concentrated NaOH and the mixture was kept at 50° C. for 20 hours.

After concentration under vacuum to half a volume, an amount of 3% by weight, referred to the volume of the mixture, of EDTA sodium salt was added, the pH was brought to 6.5–7 and the product was precipitated by addition of 2 volumes of methanol.

The product was purified by repeating two times the precipitation with methanol.

The yield by weight of oligosaccharides having an average molecular weight of 4,500 Daltons was 87.5%. The biological characteristics are shown in table 1.

EXAMPLE 2

The depolymerization process described in the preceding example was repeated by operating with identical techniques and with the same quantity of starting material and reagents.

The only variations were the incubation temperature, 40° C. instead of 50° C., and the time, 24 hours instead of 20.

The yield in oligosaccharides was 88% by weight and their average molecular weight was 3,946 Daltons. The biological activities are shown in Table 1.

EXAMPLE 3

The preceding example was repeated in identical manner, reducing the concentration of the reagents to 1/5, but keeping constant the ratios between the single reactants.

The yield was 90% and the average molecular weight was 5,590.

EXAMPLE 4

The depolymerization process described in the preceding example was repeated, but operating at a higher concentration.

25 G of heparin were treated as described in the preceding examples with 50 m.moles of ascorbic acid, 6.25 m.moles of cupric acetate and 450 m.moles of hydrogen peroxide.

The reaction mixture, the volume of which was 1 liter, contained also 100 m.moles of sodium chloride.

The yield in oligosaccharide fractions was 75% by weight and their average molecular weight was 5,986.

By comparing the results of examples 2, 3 and 4 it can be observed that, surprisingly, the best results are obtained when the heparin concentration is about 10 g/l though the molar ratios between the reagents and between these ones and the heparin remain substantially the same.

EXAMPLE 5

In order to put into evidence the differences between the methods described in the literature and the process of the present invention, the process described by S. Lasker was repeated.

(a) Depolymerization in the presence of cupric sulphate

A solution containing 2 mg/ml of heparin was incubated in the presence of ascorbic acid 4 mM, cupric sulphate 0.5 mM, sodium chloride 0.5M, sodium phosphate 0.1M at pH 7.8 for 24 hours at 40° C.

The yield in oligosaccharides was 84% in weight and the average molecular weight 9,260.

The product resulted highly polluted, in practically irreversible manner, by cupric ions.

(b) Depolymerization in the presence of hydrogen peroxide

The test described by Lasker was repeated according to the alternative method suggested by the Lasker himself and consisting in substituting the cupric sulphate with a 3% solution of hydrogen peroxide.

0.5 m.moles of hydrogen peroxide/l of solution were used instead of 0.5 m.moles of cupric sulphate. The yield in weight was 90% and the average molecular weight was 11,700.

(c) Depolymerization in the presence of cupric sulphate and hydrogen peroxide The test was still repeated by using at the same time both the cupric sulphate and the hydrogen peroxide each of them in quantities of 0.5 m.moles/l of reaction mixture.

The yield in weight was 94% and the average molecular weight was 9,150.

(d) Depolymerization in the presence of cupric sulphate and hydrogen peroxide in a solution at a concentration 5 times higher than that of above Example 5 (c)

A solution of 10 g of heparin per liter was incubated in the presence of 20 m.moles of ascorbic acid, 2.5 m.moles of cupric sulphate and 2.5 m.moles of hydrogen peroxide at 40° C. for 20 hours.

The pH was adjusted to 7.8 by means of 100 m.moles of sodium phosphate $Na_2HPO_4 \cdot 2H_2O$.

The solution contained also 500 m.moles of sodium chloride. The yield was 76% by weight and the average molecular weight was 10,936.

(e) Depolymerization in the presence of cupric sulphate and hydrogen peroxide in a solution at a concentration 12.5 times higher than that of above Example 5 (c)

The yield was 76% by weight and the average molecular weight was 12,400.

When considering the results obtained in the above given examples it appears evident that for the process of the present invention the concentration of the solution in the reaction is unexpectedly a critical factor both in order to obtain the desired average molecular weight and in order to obtain products having high ratios of antithrombotic activity/anticoagulant activity.

On the other hand corresponding concentration increases in the process derived from Lasker do not put into evidence any critic condition with reference both to the average molecular weight of the obtained oligosaccharide mixtures and to their biologic properties.

The average molecular weight was determined according to J. C. Hilborn, and P. A. Inastassiadis: Anal. Biochemistry 39, 80-92 (1971).

The anticoagulant activity was determined by means of the method described by the United States Pharmacopoeia—pag. 298–300 —USP XX and by comparison with the International Standard of Heparin WHO III.

For the anticoagulant activity, evaluated in vitro as partial activated thromboplastine time (APTT), the method of Basu D. et al., N. Eng. J. Med. 287, 1972, 324–27 was utilized.

The Xa factor inhibiting activity was evaluated by means of the coagulometric method of Denson V. W. E., Bonnar J., Thromb. Diath. Haemorr., 30, 1973, 471 or the cromogenic method of Teien A. N. et al., Thromb. Res., 8, 1976, 413.

The lipoproteinolipasic activity was evaluated by way of comparison with the House Standard by means of the method described by Bianchini P., Osi ma B., Casetta R.: Arterioscl. Journ. 5, 1967, 597; Bianchini P., Guidi G., Osima B.: Biochem. Exp. Biol. 10, 1972, 243.

Antithrombotic activity

Although the Xa factor inhibiting activity in vitro is considered in certain limits related with the antithrombotic activity, it does not necessarily predict this one.

Therefore a test was carried out relating to the inhibition of the thrombus formation in the rabbit, according to David J. L. et al. (C.R. Soc. Biol. 162, 68, 1763–66), which is considered to be suitable for the evaluation of the antithrombotic activity of a drug.

The product obtained as described in example 1 proved to be effective when administered both intravenously and orally.

| Venous thrombosis from collagen. Antithrombotic effect of LMW Heparin administered i.v. in the rabbit | | |
|---|---|---|
| Treatment mcg/kg | Dry weight of thrombus | Inhibition |
| 0 | 5.65 ± 0.31 | 0 |
| 500 | 4.19 ± 0.47 | 25.84 |
| 1000 | 2.44 ± 0.17 | 56.81 |
| 2000 | 1.72 ± 0.29 | 69.56 |

| Venous thrombosis from collagen - antithrombotic activity of LMW Hep. and Standard Hep. i.v. determination of the $ED_{50}$ values | |
|---|---|
| Treatment | $ED_{50}$ and conf. lim. USP unit/kg i.v. |
| Ep. St. | 102.52 (77.7–133.93) |
| LMW | 47.72 (36.9–61.50) |

TABLE 1

| Heparin | Average molecular weight Daltons | U.I./USP Anticoagulant activity | In vitro | | | | | In vivo | |
|---|---|---|---|---|---|---|---|---|---|
| | | | APTT | Anti-Xa coagulom. | Anti-Xa cromogenic | APTT coag. (human pl.) | Anti-Xa coag. (human pl.) | Lipoproteinolipasic activity | APTT |
| Heparin | 13500 | 139 | 170 | 135 | 105 | 124.36 ± 8.5 | 150 ± 6.9 | 28.25 | 14.33 |
| Ex. 1 | 4500 | 46 | 24.53 | 49.1 | 74 | 33.64 ± 3.47 | 201.47 ± 17.4 | 13 | 3.9 |
| Ex. 2 | 3946 | 29.1 | 15.2 | 33.12 | 61.43 | 14.11 ± 0.06 | 137.1 ± 6.26 | 7.77 | 1.9 |
| Ex. 3 | 5590 | 70.7 | 59.2 | 47.6 | 73 | 39.94 ± 0.32 | 169.77 ± 8.8 | 17.12 | 5.29 |
| Ex. 4 | 5986 | 63 | 35.74 | 54.22 | 52.97 | 34.59 ± 0.80 | 205.9 ± 16 | 12.02 | 3.16 |
| Ex. 5a | 9260 | 103.4 | 128.1 | 77.1 | 89 | 94.45 ± 7.5 | 122.24 ± 15 | n.d. | n.d. |
| Ex. 5b | 11700 | 126.2 | 165 | 111.8 | 98 | 111.19 ± 2.17 | 104 ± 7 | n.d. | n.d. |
| Ex. 5c | 9150 | 102.7 | 108.2 | 74.6 | 84 | 74.59 ± 9.03 | 121.8 ± 6.4 | n.d. | n.d. |
| Ex. 5d | 10936 | 109 | 114.9 | 90.75 | 71.49 | 75.98 ± 2.64 | 130.18 ± 3.49 | n.d. | n.d. |
| Ex. 5e | 12400 | 138 | 127 | 78.82 | 103.1 | 114.47 ± 5.17 | 119.17 ± 1.87 | n.d. | n.d. | n.d. = not determined (high M.W.)

Venous thrombosis from collagen. Antithrombotic effect of LMW Hep. administered per os in the rabbit at the dose of 200 mg/kg.

| Treatment | Unity USP/kg × $10^3$ | Dry weight of thrombus | % Inhib. of the thrombus |
|---|---|---|---|
| Control | 0 | 5.94 ± 0.82 | — |
| St. Hep. | 30.3 | 6.12 ± 0.65 | 0 |
| LMW | 9.8 | 3.17 ± 0.39 | 48.2 |

In the following Table 2 the results are shown of chemical analysis carried out on starting Heparin and on some low molecular weight (LMW) oligosaccharide fractions obtained according to the process of the present invention.

TABLE 2

| Champ. | U.A.[1] | H.A.[2] | $SO_3H$[3] | $[\alpha]^D$ 20° | Electrophoretic[4] test S-m % | F-m % |
|---|---|---|---|---|---|---|
| Heparin | 29.33 | 29.64 | 28.45 | 42 | 50 | 50 |
| Ex. 2 LMW | 24.45 | 22.50 | 25.78 | 43 | 0 | 100 |
| Ex. 3 LMW | 25.34 | 25.26 | 25.12 | 43 | 0 | 100 |

TABLE 2-continued

| Champ. | U.A.[1] | H.A.[2] | $SO_3H$[3] | $[\alpha]^D$ 20° | Electrophoretic[4] test S-m % | F-m % |
|---|---|---|---|---|---|---|
| Ex. 4 LMW | 25.58 | 20.95 | 25.20 | 42 | 0 | 100 |

[1]U.A. = Uronic Acids determined according to the method described by T. Bitter, H. Muir, Biochem. Anal. 4, 330–334, 1962.
[2]H.A. = Hexosamines determined according to the method described by N. Boas, J. Biol. Chem. 204, 533, 1953.
[3]$SO_3H$ = Sulphates determinded according to the method described by K.S. Dodyson, R.G. Price, Biochem. J. 84, 106, 1962.
[4]S-m and F-m = Slow-moving and Fast-moving fractions. The electrophoresis is carried out according to the method described by P. Bianchini et al., J. Chromatog. 196, 455–462, 1980.

I claim:

1. A process for the preparation of oligosaccharide fractions of molecular weight between 3000 and 6000 Daltons of anticoagulant activity, 20–30% of the activity of heparin and by the U.S. Patent method and anti XaCo APTT 0.6 of the value for heparin, by degradation of heparin, which consists of incubating an aqueous heparin solution containing from 5 to 20 g of heparin per liter in the presence of from 4 to 50 m.moles/l of ascorbic acid, from 0.4 to 2.5 m.moles/l of cupric acetate, and of from 50 to 300 m.moles/l of hydrogen peroxide at a temperature between 40° and 50° C. for 20–24 hours and maintaining the pH at a value between 7.5 and 8 by means of sodium acetate.

2. The process according to claim 1 wherein the process is carried out at a pH value of 7.8.

3. The process according to claim 1 wherein the aqueous heparin solution contains 10 g/l of heparin, 20 m.moles/l of ascorbic acid, 2.25 m.moles of cupric acetate, and 180 m.moles/l of hydrogen peroxide at a temperature of 50° C. for 24 hours at a pH 7.8 by means of sodium acetate.

* * * * *